(12) United States Patent
Halonen et al.

(10) Patent No.: US 11,766,626 B2
(45) Date of Patent: Sep. 26, 2023

(54) METHOD AND APPARATUS TO EXTRACT PRODUCTS FROM HEAT TREATMENT PROCESS

(71) Applicant: Oy Lunawood Ltd, Lahti (FI)

(72) Inventors: Arto Halonen, Kukkila (FI); Henry Mantsinen, Lapinlahti (FI)

(73) Assignee: OY LUNAWOOD LTD, Lahti (FI)

( * ) Notice: Subject to any disclaimer, the term of this patent is extended or adjusted under 35 U.S.C. 154(b) by 101 days.

(21) Appl. No.: 16/626,044

(22) PCT Filed: Jun. 27, 2018

(86) PCT No.: PCT/FI2018/050513
§ 371 (c)(1),
(2) Date: Dec. 23, 2019

(87) PCT Pub. No.: WO2019/002690
PCT Pub. Date: Jan. 3, 2019

(65) Prior Publication Data
US 2020/0360834 A1    Nov. 19, 2020

(30) Foreign Application Priority Data

Jun. 28, 2017  (FI) .................................... 20175615

(51) Int. Cl.
*B01D 5/00* (2006.01)
*C10B 53/02* (2006.01)
(Continued)

(52) U.S. Cl.
CPC ........... *B01D 5/0036* (2013.01); *B01D 5/006* (2013.01); *B01D 5/0057* (2013.01); *B27K 5/001* (2013.01);
(Continued)

(58) Field of Classification Search
CPC ...... C10B 53/02; B01D 5/0036; B01D 5/006; C10K 1/04; C10C 1/04; C10C 1/08;
(Continued)

(56) References Cited

U.S. PATENT DOCUMENTS 2,360,604 A   10/1944  White
4,403,948 A    9/1983  Waldmann et al.
(Continued)

FOREIGN PATENT DOCUMENTS

EP   3050943 A1 *  8/2016
JP   56-121602        9/1981
(Continued)

OTHER PUBLICATIONS

Tumuluru et al., "A Review on Biomass Torrefaction Process and Product Properties", S-1041 Symposium on Thermochemical Conversion, Oklahoma State University, Stillwater, OK, Aug. 2, 2011, URL: https://inldigitallibrary.inl.gov/sites/sti/sti/5094547.pdf (Year: 2011).*

(Continued)

*Primary Examiner* — Jonathan Luke Pilcher
(74) *Attorney, Agent, or Firm* — Nixon & Vanderhye PC

(57) ABSTRACT

The present invention relates to a method for treating a vent gas steam from heat treatment of plant biomass. The invention also relates to an apparatus for performing the method for treating a vent gas steam from heat treatment of plant biomass.

11 Claims, 2 Drawing Sheets

(51) Int. Cl.
| | |
|---|---|
| C10L 9/08 | (2006.01) |
| C10C 5/00 | (2006.01) |
| B27K 5/00 | (2006.01) |
| C07C 29/76 | (2006.01) |
| C07C 51/42 | (2006.01) |
| C07D 307/50 | (2006.01) |
| C10B 27/06 | (2006.01) |
| C11B 1/16 | (2006.01) |

(52) U.S. Cl.
CPC .............. *C07C 29/76* (2013.01); *C07C 51/42* (2013.01); *C07D 307/50* (2013.01); *C10B 27/06* (2013.01); *C10B 53/02* (2013.01); *C10C 5/00* (2013.01); *C10L 9/08* (2013.01); *C10L 9/083* (2013.01); *C11B 1/16* (2013.01)

(58) Field of Classification Search
CPC ... C10C 5/00; C10L 9/083; C10L 9/08; C07D 307/50; C11B 1/16
See application file for complete search history.

(56) References Cited

U.S. PATENT DOCUMENTS

| | | | |
|---|---|---|---|
| 4,778,585 | A | 10/1988 | Graff |
| 4,891,459 | A | 1/1990 | Knight et al. |
| 5,543,061 | A | 8/1996 | Baskis |
| 5,966,837 | A | 10/1999 | Backa et al. |
| 8,317,883 | B1* | 11/2012 | Boateng .................. C10B 53/02 44/307 |
| 8,476,480 | B1 | 7/2013 | Brown et al. |
| 2008/0006520 | A1 | 1/2008 | Badger et al. |
| 2010/0043251 | A1 | 2/2010 | Delaine |
| 2010/0223839 | A1 | 9/2010 | Garcia-Perez et al. |
| 2012/0322130 | A1 | 12/2012 | Garcia-Perez et al. |

FOREIGN PATENT DOCUMENTS

| | | |
|---|---|---|
| JP | 63-218202 | 9/1988 |
| JP | 2001-115167 | 4/2001 |
| JP | 2002-294248 | 10/2002 |
| JP | 2003-146821 | 5/2003 |
| JP | 2004-115632 | 4/2004 |
| JP | 2007-270129 | 10/2007 |
| WO | 95/15243 | 6/1995 |
| WO | 2013/019111 | 2/2013 |

OTHER PUBLICATIONS

Quang-Vu Bach, Øyvind Skreiberg, "Upgrading biomass fuels via wet torrefaction: A review and comparison with dry torrefaction", Renewable and Sustainable Energy Reviews, vol. 54, 2016, pp. 665-677, ISSN 1364-0321, https://www.sciencedirect.com/science/article/pii/S136403211501093X.*
Haiping Yang, Rong Yan, Hanping Chen, Dong Ho Lee, Chuguang Zheng, "Characteristics of hemicellulose, cellulose and lignin pyrolysis", Fuel, vol. 86, Issues 12-13, 2007, pp. 1781-1788, ISSN 0016-2361, https://www.sciencedirect.com/science/article/pii/S001623610600490X.*
Ivan Milosavljevic, Vahur Oja, and Eric M. Suuberg, "Thermal Effects in Cellulose Pyrolysis: Relationship to Char Formation Processes", Industrial & Engineering Chemistry Research 1996 35 (3), 653-662, DOI: 10.1021/ie950438l.*
Espacenet Translation of Dumas et al. (EP 3050943).*
Liang, T., and Wang, L., "Thermal treatment of poplar hemicelluloses at 180 to 220° C. under nitrogen atmosphere," (2017), BioRes. 12(1), 1128-1135.*
Webpage titled "ThermoWood", International ThermoWood Association, https://www.thermowood.fi/1.*
Espacenet English translation of Katayama et al. (JP 2004115632).*
International Search Report for PCT/FI2018/050513, dated Sep. 20, 2018, 4 pages.
Search Report for FI20175615, dated Jan. 22, 2018, 2 pages.
Office Action issued in JP Appln, No. 2019-571505 dated Dec. 2, 2020 (w/ English summary).
Office Action dated Jun. 28, 2022 in corresponding Japanese Application No. 2019-571505, 6 pages.
International ThermoWood Association—ThermoWood Handbook, Apr. 8, 2003, 66 pages.

* cited by examiner

METHOD AND APPARATUS TO EXTRACT PRODUCTS FROM HEAT TREATMENT PROCESS

This application is the U.S. national phase of International Application No. PCT/FI2018/050513 filed Jun. 27, 2018, which designated the U.S. and claims priority to FI Patent Application No. 20175615 filed Jun. 28, 2017, the entire contents of each of which are hereby incorporated by reference.

FIELD OF THE INVENTION

The invention relates to a method for treatment of vent gas steam from heat treatment of plant biomass. The invention also relates to an arrangement for performing the method.

BACKGROUND OF THE INVENTION

Heat treatment of plant biomass causes the biomass to undergo permanent changes in physical and chemical properties. Material is released and removed from the biomass—for example covalently bound water is removed as steam. The heat treatment also forms and releases from the biomass small oxygen containing organic molecules such as methanol and acetic acid and releases naturally occurring chemical compounds and substances from the processed biomass. Heat treated biomass such as wood is resistant to moisture and temperature changes and is applicable for various purposes.

The material released from biomass during heat treatment is partly in gaseous (gaseous or aerosol) form and is typically removed as vent gas and disposed. Part of released material is in liquid form, flowing to bottom of the heat treatment chamber where it is typically drained away from the chamber and disposed.

Heat treatment involves displacing enough oxygen by a shielding gas to prevent combustion or partial oxidation of processed material by oxygen. The shielding gas may be steam i.e. gaseous water. When the solid material to be processed as well as heat and water in the form of steam or liquid water for cooling are put into the process, the water for cooling instantly vaporizes to form steam in the temperature used in the heat treatment process.

Heat treatment produces an exhaust stream of vent gas steam that comprises material released from the biomass. One of the disadvantages associated with conventional arrangements is that the material released from biomass and comprised in the vent gas steam is disposed and the valuable components contained in it are not utilized. A further disadvantage is that some of the components of the disposed material may be harmful to the environment.

BRIEF DESCRIPTION OF THE INVENTION

An object of the present invention is to provide a method for treatment of vent gas steam from heat treatment of plant biomass and an arrangement for performing the method so as to overcome the above mentioned disadvantages.

The objects of the invention are achieved by a method and an arrangement which are characterized by what is stated in the independent claims. Preferred embodiments of the invention are disclosed in the dependent claims.

The invention is based on the realization that by utilizing a series of condensers operated at different temperatures with the temperature in each condenser being lower than in the previous condenser, material contained in the vent gas steam can be selectively separated to fractions.

In an embodiment, the method of treating a vent gas steam from heat treatment of plant biomass, comprises the steps of:
heat treating plant biomass in a heat treatment chamber,
directing the vent gas steam from the heat treatment to a series of condensers connected to each other to provide flow of the vent gas steam through the entire series,
collecting at least part of the components of the vent gas steam in each condenser,
wherein each of the condensers is set at a temperature that is lower than the temperature in the previous condenser in the series, and
wherein the first condenser in the series is set at a temperature that is lower than the temperature in the heat treatment chamber.

An advantage of the invention is that products can be selectively fractionated from the vent gas steam to provide a variety of refined valuable products that may be utilized as such or further treated to yield usable products.

A further advantage of the invention is that materials released from the biomass are not released to the environment but are recovered in a controlled manner.

BRIEF DESCRIPTION OF THE DRAWINGS

In the following the invention will be described in greater detail by means of preferred embodiments with reference to the accompanying drawings, in which.

DETAILED DESCRIPTION OF THE INVENTION

Figure 1:
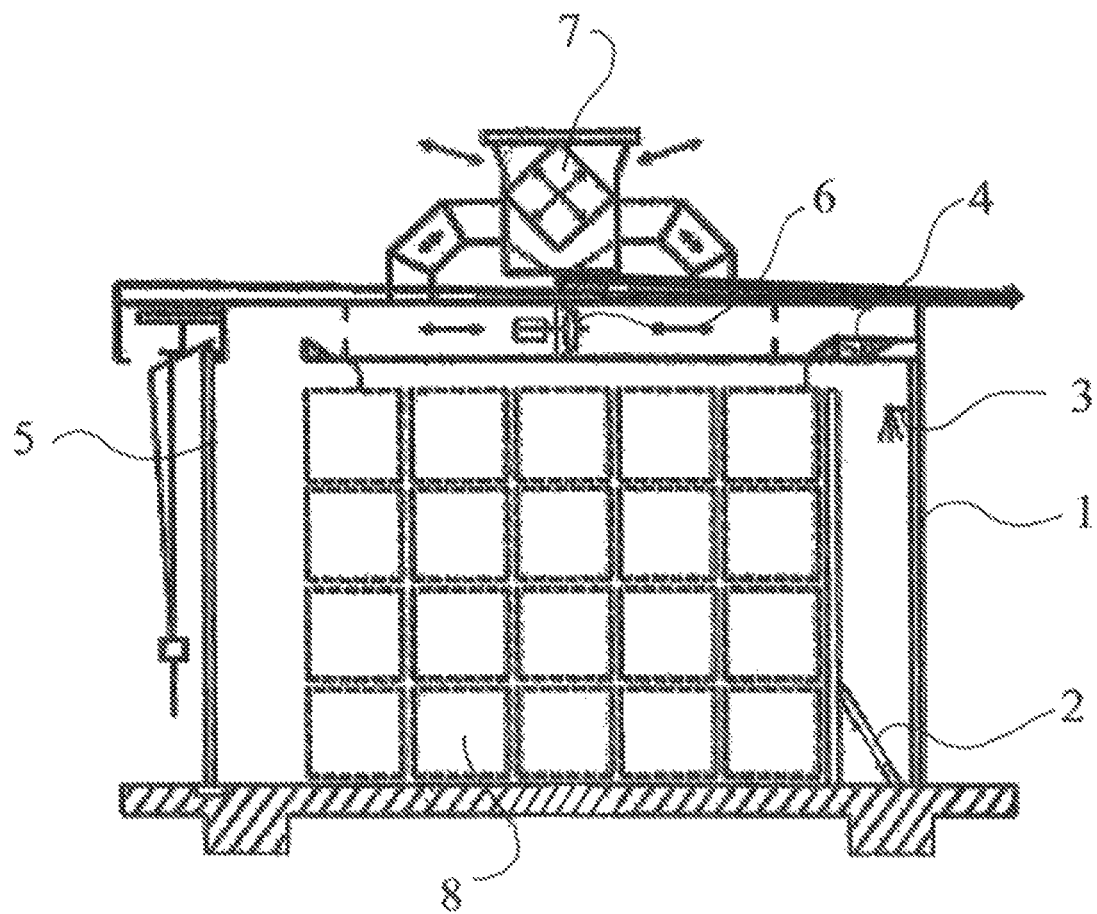
FIG. 1 shows a schematic view of an exemplary illustration of an apparatus for heat treating plant biomass.

The invention is based on a method for treatment of vent gas steam from heat treatment of plant biomass.

Heat treatment produces from the heat treatment chamber an exhaust stream of vent gas steam. Vent gas steam is a gaseous (gas, aerosol) material that comprises material released from the biomass.

It has surprisingly been discovered that vent gas steam can be treated to produce solid (at room temperature) or liquid products by fractionating the vent gas steam in a condenser apparatus. Vent gas steam is directed from the heat treatment chamber to a condenser apparatus comprising a series of several condensers, preferably three or more condensers, set to different temperatures. In the condenser series, the temperature of a condenser is higher than the temperature of the condenser that is next in the series. Thus, specific products may be collected from the vent gas steam at specific process timeframes and condenser temperatures.

In an embodiment, the method for treating vent gas steam comprises the following steps:
heat treating plant biomass in a heat treatment chamber,
directing the vent gas steam from the heat treatment to a series of condensers connected to each other to provide flow of the vent gas steam through the entire series,
collecting at least part of the components of the vent gas steam in each condenser, wherein each of the condensers is set at a temperature that is lower than the temperature in the previous condenser in the series, and wherein the first condenser in the series is set at a temperature that is lower than the temperature in the heat treatment chamber.

In an embodiment, the series of condensers comprises three or more condensers. In another embodiment, the series of condensers comprises three to six condensers. In another embodiment, the series of condensers comprises four condensers. In another embodiment, the series of condensers comprises five condensers. In another embodiment, the series of condensers comprises six condensers.

When biomass is heat treated between a temperature of about 160° C. and a temperature below the point where carbonization begins to occur, defined as before initiation of exothermal degradation of cellulose, the biomass undergoes permanent changes in qualities such as composition and structure. The temperature where material starts to exothermally degrade varies with the material in question, being typically between 260° C. to 300° C. for different types of plant biomass.

In an embodiment, the heat treatment of plant biomass is performed at a temperature of 160° C. to 300° C.

In another embodiment, the plant biomass is wood.

Prior to heat treatment, the biomass may be dried at a temperature of up to 150° C. as a part of the process to achieve a fixed moisture content. In an embodiment, the biomass may be dried at a temperature of 100° C. to 150° C.

When steam is used as a shielding gas to prevent combustion or partial oxidation of processed biomass by oxygen, vent gas steam further comprises steam used in the process as a shielding gas. Steam may be fed to heat treatment from a separate system or apparatus that applies heat to water to produce steam, or may be generated in situ by adding liquid water for vaporization to steam within the heat treatment chamber.

In an embodiment, steam is used as a shielding gas in the heat treatment.

The heat treatment process induces physical and chemical changes in the processed biomass, the chemical changes including, but not being limited to, release of covalently bound water and formation of small oxygen containing organic molecules such as acetic acid and methanol. The effects of heat treatment also include removal of material that has been released or modified or formed from the processed biomass. In addition, some of material occurring naturally in unmodified form or as a product of heat treatment process is removed the processed biomass by the principle of steam distillation that affects boiling and condensation temperatures of mixtures of two or more of immiscible phases where water forms the majority of one of the immiscible phases of a complex continuous series of mixture(s) released from biomass during heat treatment. Steam distillation requires that steam i.e. water vapour is maintained at a temperature of above 100° C. during heat treatment.

In the heat treatment process, a long duration temperature program lasting up to tens of hours and causing physical and chemical changes that occur over time and temperature changes leads to sequential release of material to gaseous phase at different time frames. For compounds with high boiling points, the sequential release may occur at a temperature that is significantly lower than the boiling point of the compound.

Compounds comprised in the material that is released from the biomass to gaseous phase and carried in the vent gas steam may thus be separated at specific process time frames. It follows that compounds may be collected as fractionated, essentially refined products by sequential condensation in a condenser apparatus comprising a series of condensers operated at specific temperatures.

It has surprisingly been discovered that in sequential condensation where compounds that are released at same or overlapping timeframe based on their respective boiling points are collected in a series of condensers, compounds condensed at previous condenser are not carried in significant amounts to the next condenser when the temperature is higher in the previous condenser than in the next condenser.

In the method of the invention, sequential condensation may yield products with no or little impurities, causing the use or refinement of the products to require no additional procedures such as dewatering or distillation. Each condensate in sequential condensation may consist of one, two or several inmiscible phases which are optionally separated by decanting.

In the method of the invention, conditions may be tailored according to qualities such as origin, composition and texture of the plant biomass in question. For example, the temperature where material starts to exothermically carbonize varies with the plant biomass in question, being typically between 260° C. to 300° C. for different types of plant biomass. The temperature selected for heat treatment affects the composition of the material released from the biomass i.e. the selection and amount of substances and compounds within the released material. Also properties such as plant species, part of plant treated, particle size and moisture content of the biomass may affect the selection of method conditions through changes in the release timeframe and temperature as well as types and amounts of compounds released from the biomass.

The method of the invention involves control of a heat treatment apparatus and a condenser apparatus, including, but not limited to, control of rate of heating in heat treatment process, rate of steam fed to process and temperatures of condensers. All of these process parameters are controlled at any specific timepoint(s) or -frame(s) of the process.

The heat treatment chamber pressure is limited by prevention of condensation by pressure drop at chamber exit. In the condenser system, the pressure is typically few tens of millibars above ambient. Also working against backpressure of condenser system is feasible.

Flow rate (kg/h) in the process varies depending on treatment chamber size, process parameters and stage of the process. Flow rate is also dependent on rate of shielding gas steam fed to the heat treatment chamber. When the first condenser in the series that is set at a temperature of below 100° C. is reached, the flow rate drops by more than 90%. The drop of flow rate may act as an exhauster if back flow is prevented or a vacuum pump is placed after the first condenser in the series that is set at a temperature of below 100° C.

In an embodiment, the first condenser in the series is set at a temperature of above 100° C. and the next condenser(s) is (are) set at a temperature of below 100° C.

In another embodiment, the first condenser in the series is set at a temperature of at least 100° C. and the next condenser(s) is (are) set at a temperature of below 100° C.

In another embodiment, the condenser series comprises at least two condensers set at a temperature of above 100° C. and at least one condenser set at a temperature of below 100° C.

In another embodiment, the condenser series comprises at least two condensers set at a temperature of at least 100° C. and at least one condenser set at a temperature of below 100° C.

In the heat treatment process, mainly three types of condensate i.e. phases are formed. Phase 1 is a so called wood vinegar phase, an aqueous phase including a plurality of other compounds at varying concentrations. Phase 1 is a wood vinegar (EC 232-450-0, CAS 8030-97-5)-like substance. Phase 2 is a terpene phase, a yellowish, fluid phase that is immiscible with water and comprises alpha-pinene and other isoprene polymers. Phase 3 is a tar phase, a dark-coloured phase that is immiscible with water and mostly not soluble in the wood vinegar or terpene phases. All phases 1 to 3 are formed during the entire heat treatment, but their composition and relative proportions change.

The first condenser set at a temperature of above 100° C. may condense phases 1 and 3. The next condenser(s) set at a temperature of below 100° C. may condense phases 1 and 2.

In another embodiment the condenser series comprises condenser(s) set at a temperature above 130° C., condenser(s) set at a temperature of above 100° C. to 120° C. and condenser(s) set at a temperature of below 100° C.

In yet another embodiment the condenser series comprises condenser(s) set at a temperature of 120° C. to 160° C., preferably 120° C. to 140° C., more preferably 130° C.; condenser(s) set at a temperature of above 100° C. to 120° C., preferably 105° C. to 115° C., more preferably 105° C.; condenser(s) set at a temperature of 80° C. to below 100° C., preferably 80° C. to 95° C., more preferably 90° C.; and condenser(s) set at a temperature of 20° C. to 60° C., preferably 20° C. to 40° C., more preferably 30° C.

In yet another embodiment the condenser series comprises condenser(s) set at a temperature of 120° C. to 140° C.; condenser(s) set at a temperature of 105° C. to 115° C.; condenser(s) set at a temperature of 80° C. to below 100° C.; and condenser(s) set at a temperature of 20° C. to 60° C.

In yet another embodiment the condenser series comprises condenser(s) set at a temperature of 130° C.; condenser(s) set at a temperature of 105° C.; condenser(s) set at a temperature of 90° C.; and condenser(s) set at a temperature of 30° C.

In yet another embodiment the material contained in the vent gas steam is recovered when the heat treatment temperature is above 180° C. In this case significant amounts of various substances and compounds have been released from the plant biomass.

When the heat treatment temperature is 180° C. to 200° C., the first condenser set at a temperature of above 100° C. may condense a non-water soluble high purity tall oil (EC 232-304-6, CAS 8002-26-4)-like substance that is a part of phase 3, the tar phase, and comprises a limited amount of various fatty acids and resin acids. At a heat treatment temperature above 200° C., the tall oil-like fraction further comprises plant sterol-like compounds.

The next condenser in the series set at a temperature of above 100° C. may produce a wood vinegar (EC 232-450-0, CAS 8030-97-5)-like substance. The condenser next in the series that is the first condenser set at a temperature of below 100° C. may produce wood vinegar and terpene phases, turpentine, as well as a small amount of water-methanol mixture, methyl acetate and similar low boiling poorly water miscible esters and ethers.

The invention is also based on an arrangement for performing treatment of vent gas steam from heat treatment of plant biomass. The arrangement comprises a heat treatment chamber for heat treating plant biomass to produce a vent gas steam, a series of condensers, an exhaust tube to direct the vent gas steam from the heat treatment chamber to the first condenser, and piping to connect the condensers in the condenser series to each other. During heat treating plant biomass, the apparatus is configured to set the temperature of each condenser in the series of condensers to be lower than the temperature in the previous condenser in the series, and to set the temperature of the first condenser in the series of condensers to be lower than the temperature in the heat treatment chamber. The apparatus may also comprise a system and a conduit to provide steam to the heat treatment chamber.

The exemplary arrangement illustrated in FIG. 1 comprises a heat treatment chamber 1 where the biomass is placed for heat treatment and an exhaust tube 2 to remove liquid from the heat treatment chamber. Optionally, the arrangement comprises a system and a conduit 3 to provide steam to the heat treatment chamber. The arrangement also comprises a piping 4 for hot oil and a bank of hot oil boilers 5 to provide heat to the heat treatment chamber, a blower unit 6 to circulate gas in heat treatment chamber and an exhaust tube 7 for vent gas steam.

Figure 2:
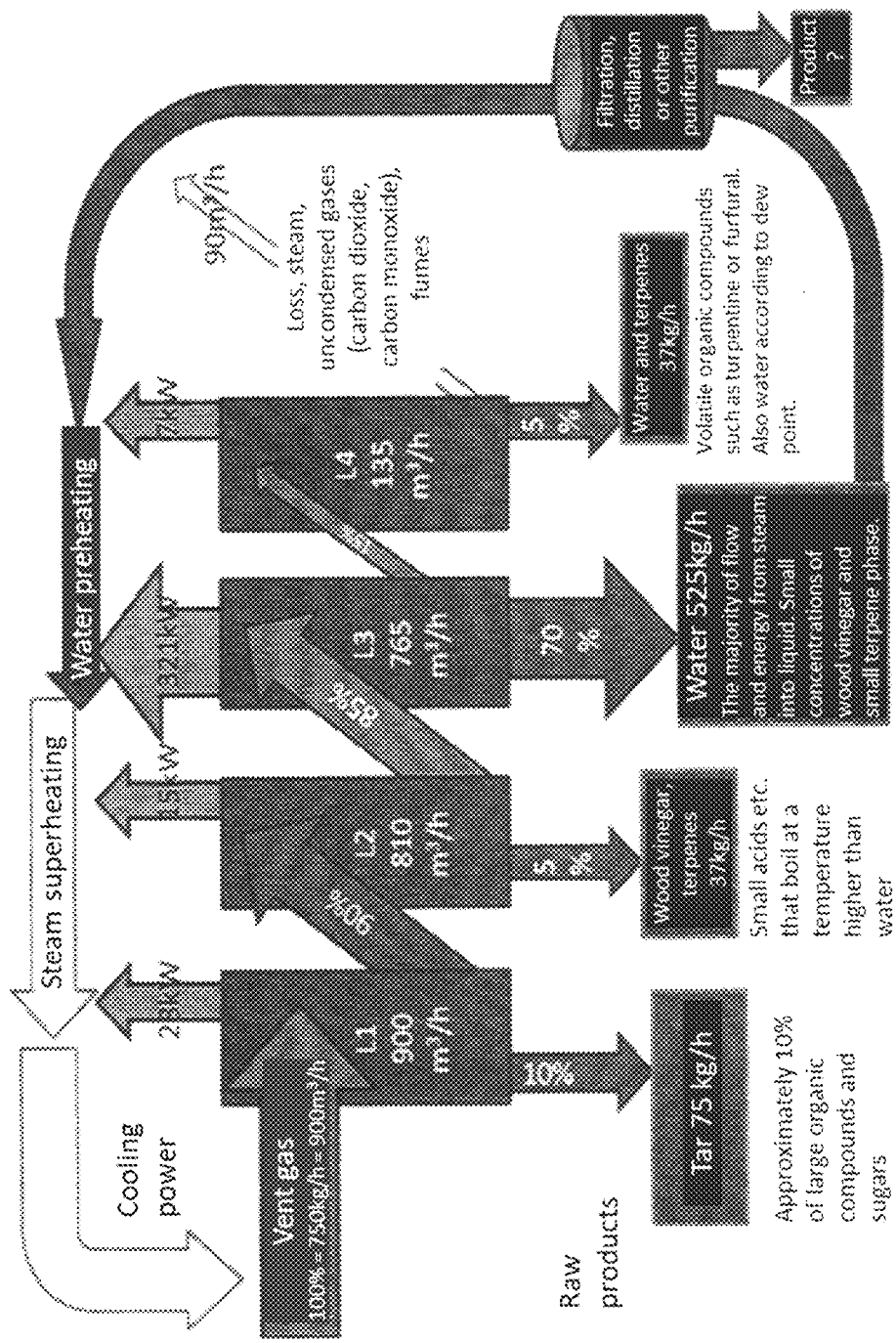
FIG. 2 is a schematic view of an exemplary illustration of a condenser apparatus comprising a series of condensers for treating vent gas steam. Steam volumes of condensers L1 to L4 are reported under normal temperature and pressure (NTP) conditions.

The exemplary arrangement further comprises a condenser apparatus comprising a series of condensers connected to each other with piping to recover at least a part of the material contained in the vent gas steam. The exemplary condenser apparatus illustrated in FIG. 2 comprises a series of four condensers L1, L2, L3 and L4. The first condenser L1 in the series is connected to exhaust tube 7 of the heat treatment chamber to direct the vent gas steam to the series of condensers. All condensers in the series are connected to each other with piping. Condenser L1 has a higher temperature than condenser L2 which has a higher temperature than L3 which in turn has a higher temperature than L4. Thus, each condenser may collect substantially different compounds and substances from the vent gas steam as the temperature gradually decreases while the vent gas steam is passed through the series of condensers.

In an embodiment, the series of condensers comprises three or more condensers. In another embodiment, the series of condensers comprises three to six condensers. In another embodiment, the series of condensers comprises four condensers. In another embodiment, the series of condensers comprises five condensers. In another embodiment, the series of condensers comprises six condensers.

In another embodiment, the majority of material comprised in the vent gas steam is recovered in the condenser apparatus.

When using the arrangement according to FIG. 1, plant biomass 8 is placed in the heat treatment chamber 1 for heat treatment.

The condensers are operated at a temperature where each previous condenser is at a higher temperature that the next condenser in the series. In the exemplary arrangement illustrated in FIG. 2, condenser L1 recovers as a tar phase larger compounds that condense before acetic acid such as large organic compounds and other high boiling point organic compounds. The condenser L1 is designed in such a manner that 750 kg/h of steam (of which 500 kg/h is steam fed to heat treatment) may flow through without much back pressure. Condenser L2 condenses as a wood vinegar phase and as a terpene phase organic compounds that have a boiling point higher than that of water, but leaves water in gaseous phase. The condenser L2 is designed in such a manner that 700 kg/h of steam (of which 500 kg/h is steam fed to heat treatment) may flow through without much back pressure. Condenser L3 condenses water as a dilute wood vinegar phase, a terpene phase and small concentrations of other compounds, and flow decreases from a level of 800 m$^3$/h to a level of 150 m$^3$/h. Condenser L4 condenses as a terpene phase and as an aqueous phase compounds such as volatile organic compounds, terpenes, methanol, methyl acetate (some of which are immiscible to water) and water according to dew point. Condenser L4 condenses vent gas steam at the level of dew point, and flow decreases to a level of less than 100 m$^3$/h. The condensates collected from the condensers may optionally be filtered, distilled or purified in other manner to recover any desired substances or compounds.

In an embodiment, the arrangement of the invention is configured to perform the method of the invention.

EXAMPLES

Example 1. Simplified System with Sampling Method

A heat treatment was performed to sawn timber samples of Norway spruce (*Picea abies*) and Scots pine (*Pinus sylvestris*). The samples were of two different physical dimensions, thick and thin. Heat treatment of each four types of wood samples was performed as duplicates. Thus, a total of eight heat treatments were performed.

The heat treatment was performed according to Thermo-D class product treatment using steam as a shielding gas and comprised the following steps: increasing temperature first rapidly to about 100° C. and then more slowly to about 130° C. to remove the majority of moisture from the wood, heat treating by first gradually increasing the temperature to 200° C. and then holding the temperature at >200° C., and cooling by decreasing the temperature by water spraying.

Sampling was performed from a condenser apparatus consisting of two condensers connected in a series, first condenser L1 at 110° C. and second condenser L2 at 30° C. Each of the eight processes was sampled i) during increase of temperature from 180° C. to 200° C. and ii) during holding the temperature at >200° C. until end of the holding phase, before the cooling phase was started. A sample was collected from both condensers L1 and L2 during each of the phases i) and ii).

Sample collection was performed from vent gas steam exhaust tube, where a small part of vent gas steam flow was directed through a branch pipe via an expansion tank to the condenser apparatus, and the exhaust gases from the condensers were further directed to outdoor air. Main part of vent gas steam was under suction of a transfer blower. In the first three collections the branch pipe was led as directly as possible to the outside of the exterior wall of the heat treatment chamber room and thereon downwards, and the expansion tank and condensers were attached to the exterior wall on the outside of the heat treatment chamber room, and the bottom of the expansion tank was uninsulated. In the remaining five collections the branch pipe, expansion tank and condensers were placed on the inside of the exterior wall of the heat treatment chamber room, in a hallway between the room and the exterior wall. In this case also the entire expansion tank was insulated and the entire arrangement was thus protected from weather and the cooling effect of wind.

In addition to samples collected from condensers L1 (110° C.) and L2 (30° C.), a compilation sample was collected from the bottom of the expansion tank as a significant amount of liquid was noted to collect there. The surface temperature of the exhaust tube before the closing cock, about 20 cm from the main tube insulation varied between 110° C. and 170° C. depending on the process phase and branch pipe flow, but temperature of the vent gas steam entering condenser L1 was typically 90° C. to 98° C. This meant that compounds with boiling points above this temperature were mainly collected in the compilation sample.

The sample collection yielded samples i) and ii) from both condensers L1 and L2 as well as the compilation sample from the expansion tank. Thus, a total of 5 samples were obtained from each of the eight heat treatments, each sample typically containing at least two phases. Total amount of samples from all experiments was thus 80, consisting of 10 different phase samples from each of the eight different heat treatments.

With the above described sampling system three different phases could be separated from the samples: an oily terpene phase (2) that comprises terpenes and is lighter than water; a water-containing wood vinegar phase (1) with significant concentrations of other compounds; and a tar phase (3) that is black in colour, has a varying fluidity and a complex composition. Phases 1 and 3 were present in the compilation sample and in samples collected from condenser L1, and phases 1 and 2 were present in samples collected from condenser L2.

It was also typical that the collection time was shorter for thin than thick wood, and longer for spruce than pine.

The collection succeeded well and with it a sample material was collected from vent gas steam of heat treated wood production process. The fraction with largest volume was the wood vinegar phase, an aqueous fraction containing various water-soluble compounds as a concentration of several percent of total volume. The water fraction may have commercial value in itself or as further refined products. Also significant is the terpene phase, an oily fraction from pine which may be used as such. Also the tar fraction comprises commercially usable compounds, and tar itself is a usable product.

The collected samples comprised 91 vol-% to 97 vol-% of water or compounds dissolved in water such as acetic acid, formic acid, methanol and furfural. Oily fraction i.e. terpene phase formed less than 1 vol-% of vent gas steam from spruce samples, but about 5 vol-% of vent gas steam from pine samples. Terpene phase made up approximately 10 vol-% of condensate from condenser L2. Tar phase made up on average 2 vol-% to 4 vol-% of the volume of the total collected water phase. Acetic acid made up on average 3.3 vol-% of the total volume of the water phase and approximately 3.1 vol-% of the total volume of collected liquid material. Furfural made up on average 0.7 vol-% of the total volume of the water phase and approximately 0.6 vol-% of the total material. Terpene phase made up approximately 4 vol-% of the total volume of collected liquid material.

In addition to water, compounds obtainable from the aqueous phase are the main components such as acetic acid, methanol and furfural. The terpene phase may be used as such either as a chemical or source of energy. When the temperature of the wood exceeds 170° C. in the process, the terpene phase may make up up to 10 vol-% of the liquid volume that condenses at temperatures below 100° C. Also other compounds may be recovered and used, as these compounds number in hundreds or thousands.

Example 2. Complex Collection System with Sampling Method

A heat treatment was performed to sawn timber samples of Scots pine (*Pinus sylvestris*). The samples were of thick physical dimension, and the heat treatment was performed twice for the same sample using different sampling systems. The heat treatment was performed as in Example 1.

The first process was sampled from 110° C. until end of holding phase and in cooling stage down to 112° C. Sample collection vessels were changed at a cut-off temperature of 170° C., at the end of holding phase and at the end of cooling phase. Sample collection vessels were also changed during the process whenever they reached full capacity.

The second process was sampled from 170° C. until end of the holding phase i.e. before cooling phase was started. Sample collection vessels were changed during the process whenever they reached full capacity.

Sampling was performed from a condenser apparatus consisting of six condensers L1 to L6 connected in a series, first condenser L1 operated at 140° C., second condenser L2 at 120° C., third condenser L3 at 105° C., fourth condenser L4 at 90° C., fifth condenser L5 at 60° C. and sixth condenser L6 at 10° C. Samples were collected from each condenser separately, each sample from each condenser typically containing two phases. Total volume of samples collected during the first process was about 38 liters, and about 25 liters during the second process.

Sample collection was performed from vent gas steam exhaust tube, where a small part of vent gas steam flow was directed through a heated branch pipe via an expansion tank to the condenser apparatus, and the exhaust gases from the condenser apparatus were further directed to outdoor air. During sampling from the first process the transfer blower was offline and vent gas steam vented against ambient air. During sampling from the second process main vent gas steam was under suction of the transfer blower. Between the first and second process processes, a pressure difference of several tens of pascals was noticed between main pipe and branch pipe exits. The pressure difference was caused by use of the transfer blower in the second process. The pressure difference was the main cause of the difference in total sample volume collected from the two processes.

The outer surface temperature of the vent gas steam exhaust tube under insulation before closing cock varied between 110 and 170° C. depending on process stage. Temperature of the vent gas steam flow stabilized to around 120° C. to 150° C. in the branch pipe before entering the condenser apparatus.

At a heat treatment temperature between 180° C. to 200° C., condensate from condenser L1 was a high purity (as determined by light colour and IR spectra) tall oil-like substance. At a heat treatment temperature above 200° C. there were small amounts of plant sterol-like compounds included in the tall oil.

Volumes of liquid collected from condensers L1, L2 and L3 each were about 5 vol-% to about 10 vol-% of total volume of liquid collected. Samples from condensers L2 and L3 contained an oily terpene fraction and an aqueous wood vinegar phase. Samples from condensers L1 to L3 contained small amounts of water due to cold spots in collector apparatus.

The majority of total condensate volume was collected in condensers L4 and L5. The volume of liquid collected from L4 made up approximately 50 vol-% of total volume of liquid collected. The largest fraction of condensates in both L4 and L5 was an aqueous wood vinegar phase with dissolved acids, alcohols, furfural and other small oxygen containing compounds. A significant second phase of terpenes was also present. At temperatures above 180° C. when steam/water feed in the heat treatment was at peak, capacity of L4 was exceeded and part of aqueous phase condensed in L5.

Condenser L6 had only trace amounts of condensate, and in some cases none.

Based on results of Examples 1 and 2 it can be concluded that a two condenser system may not achieve enough separation, while a six condenser system may have some redundancy and unnecessary capacity. Process parameters, quality of plant biomass to be treated and the types of products that are sought after affect the number of condensers required to achieve a desired result. The number of condensers required may exceed six condensers.

Ready-made solutions are on the market for separating small oxygen containing molecules from aqueous material that may be applied for further processing of the aqueous condensates of the invention.

The purified water may be reused according to principles of circular economy either by distilling it to steam to be used in the process whereupon it can be purified from compounds that have a boiling point higher than water and/or by filtering e.g. by reverse osmosis, whereby the more concentrated solution contains usable substances or compounds.

It will be obvious to a person skilled in the art that as the technology advances, the inventive concept can be implemented in various ways. The invention and its embodiments are not limited to the examples described above but may vary within the scope of the claims.

The invention claimed is:

1. A method of treating a vent gas steam from heat treatment of plant biomass, the method comprising:
    heat treating plant biomass in a heat treatment chamber at a temperature between 160° C. and a temperature that is below a point where carbonization begins to occur, defined as before initiation of exothermal degradation of cellulose, using a shielding gas in the heat treatment, the shielding gas being steam, the steam being water vapor,
    directing the vent gas steam from the heat treatment to a series of condensers connected to each other to provide flow of the vent gas steam through each condenser in the series,
    collecting at least part of the components of the vent gas steam in each condenser,
    wherein each of the condensers is set at a temperature that is lower than the temperature in the previous condenser in the series,
    wherein a first condenser in the series is set at a temperature that is lower than the temperature in the heat treatment chamber,
    wherein the series of condensers comprises at least two condensers set at a temperature of above 100° C. and at least one condenser set at a temperature of below 100° C., wherein the at least two condensers produce a tar phase and a wood vinegar phase, and the at least one condenser produces a wood vinegar phase and a terpene phase, and
    wherein the plant biomass is not carbonized in the heat treatment.

2. The method as claimed in claim 1, wherein the first condenser and a second condenser in the series of condensers are set at a temperature of above 100° C. and the next condenser(s) in the series is (are) set at a temperature of below 100° C.

3. The method as claimed in claim 1, wherein the series of condensers comprises at least one condenser set at a temperature above 130° C., at least one condenser set at a temperature of above 100° C. to up to 120° C., and at least one condenser set at a temperature of below 100° C.

4. The method as claimed in claim 1, wherein the plant biomass is wood.

5. The method as claimed in claim 1, wherein the plant biomass is dried prior to heat treatment.

6. A method of treating a vent gas steam from heat treatment of plant biomass, the method comprising:
heat treating plant biomass in a heat treatment chamber at a temperature between 160° C. and a temperature that is below a point where carbonization begins to occur, defined as before initiation of exothermal degradation of cellulose, using a shielding gas in the heat treatment, the shielding gas being steam, the steam being water vapor,
directing the vent gas steam from the heat treatment to a series of condensers connected to each other to provide flow of the vent gas steam through each condenser in the series,
collecting at least part of the components of the vent gas steam in each condenser,
wherein each of the condensers is set at a temperature that is lower than the temperature in the previous condenser in the series,
wherein a first condenser in the series is set at a temperature that is lower than the temperature in the heat treatment chamber, and
wherein the series of condensers comprises at least two condensers set at a temperature of above 100° C. and at least one condenser set at a temperature of below 100° C., wherein the at least two condensers set at the temperature of above 100° C. are operated to produce a tar phase and a wood vinegar phase, and the at least one condenser set at the temperature of below 100° C. is operated to produce a wood vinegar phase and a terpene phase.

7. The method as claimed in claim 6, wherein the first condenser and a second condenser in the series of condensers are set at a temperature of above 100° C. and the next condenser(s) in the series is (are) set at a temperature of below 100° C.

8. The method as claimed in claim 6, wherein the series of condensers comprises at least one condenser set at a temperature above 130° C., at least one condenser set at a temperature of above 100° C. to up to 120° C., and at least one condenser set at a temperature of below 100° C.

9. The method as claimed in claim 6, wherein the plant biomass is wood.

10. The method as claimed in claim 6, wherein the plant biomass is dried prior to heat treatment.

11. The method as claimed in claim 6, wherein the phases are produced as condensates during the heat treatment.

* * * * *